(12) United States Patent
Breiwa, III

(10) Patent No.: US 12,127,601 B2
(45) Date of Patent: Oct. 29, 2024

(54) METHOD OF VOLATIZING A SUBSTANCE

(71) Applicant: Dynavap, LLC, DeForest, WI (US)

(72) Inventor: George R. Breiwa, III, Dane, WI (US)

(73) Assignee: Dynavap, LLC, DeForest, WI (US)

( * ) Notice: Subject to any disclaimer, the term of this patent is extended or adjusted under 35 U.S.C. 154(b) by 922 days.

(21) Appl. No.: 17/031,513

(22) Filed: Sep. 24, 2020

(65) Prior Publication Data
US 2021/0008242 A1     Jan. 14, 2021

Related U.S. Application Data

(62) Division of application No. 14/142,351, filed on Dec. 27, 2013, now Pat. No. 11,213,073.

(51) Int. Cl.
| | |
|---|---|
| *A24F 40/60* | (2020.01) |
| *A61L 9/03* | (2006.01) |
| *A61M 15/06* | (2006.01) |
| *H05B 1/02* | (2006.01) |
| A24F 40/20 | (2020.01) |
| A61M 11/04 | (2006.01) |

(52) U.S. Cl.
CPC ............... *A24F 40/60* (2020.01); *A61L 9/03* (2013.01); *A61M 15/06* (2013.01); *H05B 1/0291* (2013.01); *A24F 40/20* (2020.01); *A61M 11/042* (2014.02); *A61M 11/047* (2014.02); *A61M 11/048* (2014.02); *A61M 2205/583* (2013.01)

(58) Field of Classification Search
CPC ............ A24F 40/20; A24F 40/60; A61L 9/03; A61M 11/042; A61M 11/047; A61M 11/048; A61M 15/06; A61M 2205/583; H05B 1/0291

USPC ................................................. 392/386–406
See application file for complete search history.

(56) References Cited

U.S. PATENT DOCUMENTS

| | | | |
|---|---|---|---|
| 1,515,222 A | * | 11/1924 | Ruben ...................... F01P 11/16 |
| | | | 374/146 |
| 4,774,971 A | | 10/1988 | Vieten |
| 5,591,368 A | | 1/1997 | Fleischhauer |
| 5,743,251 A | | 4/1998 | Howell |
| 5,878,752 A | | 3/1999 | Adams |

(Continued)

FOREIGN PATENT DOCUMENTS

| | | |
|---|---|---|
| CN | 101500443 | 8/2009 |
| JP | 2010-520742 | 6/2020 |

(Continued)

OTHER PUBLICATIONS

PCT/US2013/078067 filed Dec. 27, 2013, International Search Report and Written Opinion of the International Searching Authority dated May 20, 2014, 13 pgs.

*Primary Examiner* — Sang Y Paik
(74) *Attorney, Agent, or Firm* — Boardman & Clark LLP

(57) ABSTRACT

A volatizer is provided including a multifunction cap secured over the open end of a body or other device, the chamber or other part of the device holding an amount of material to be extracted by selective volatization therein and including a thermo-indicator thereon or therein capable of deforming, actuating or otherwise indicating upon heating to a preselected temperature to provide an indication of the proper temperature for volatilization and extraction of the selected and or target compound from the material within the device. Also provided is a method of volatizing a substance.

10 Claims, 6 Drawing Sheets

(56) References Cited

U.S. PATENT DOCUMENTS

| | | | |
|---|---|---|---|
| 6,095,153 | A | 8/2000 | Kessler et al. |
| 6,164,287 | A | 12/2000 | White |
| 7,173,222 | B2 | 2/2007 | Cox et al. |
| 7,370,435 | B2 | 5/2008 | Boki |
| 7,434,584 | B2 | 10/2008 | Steinberg |
| 8,430,106 | B2 | 4/2013 | Potter |
| 2002/0078956 | A1* | 6/2002 | Sharpe ................. A61M 11/042 128/203.26 |
| 2003/0033055 | A1 | 2/2003 | McRae |
| 2004/0031495 | A1 | 2/2004 | Steinberg |
| 2006/0196518 | A1 | 9/2006 | Hon |
| 2007/0074734 | A1 | 4/2007 | Braunshteyn |
| 2008/0057218 | A1 | 3/2008 | Gregg |
| 2009/0032034 | A1 | 2/2009 | Steinberg |
| 2010/0059070 | A1* | 3/2010 | Potter .................... A24F 42/60 131/194 |
| 2011/0036346 | A1 | 2/2011 | Cohen |
| 2013/0042865 | A1 | 2/2013 | Monsees |
| 2014/0283860 | A1 | 9/2014 | Stoltz |

FOREIGN PATENT DOCUMENTS

| | | |
|---|---|---|
| KR | 2012089544 | 6/2011 |
| WO | WO 2007143993 | 12/2007 |

\* cited by examiner

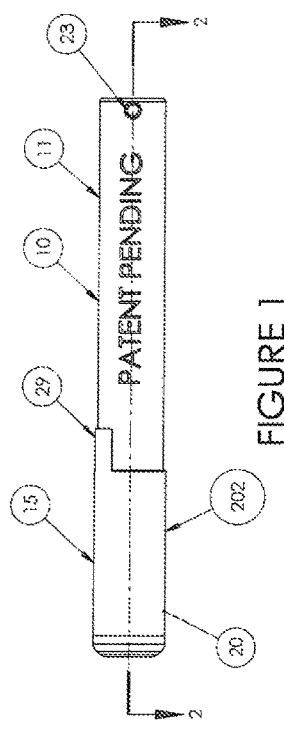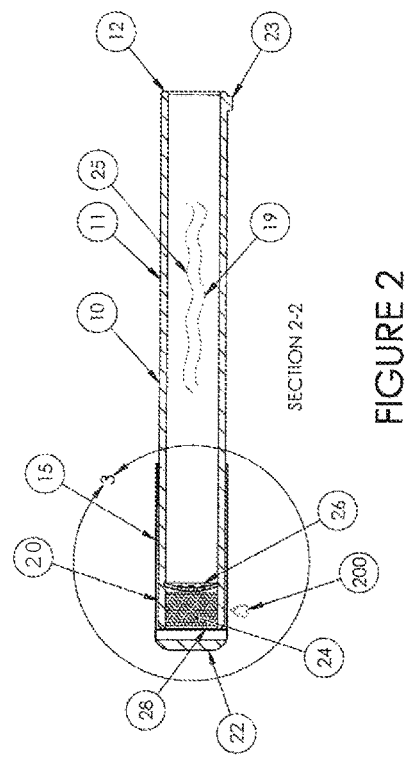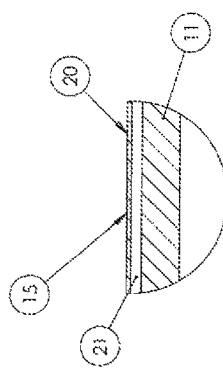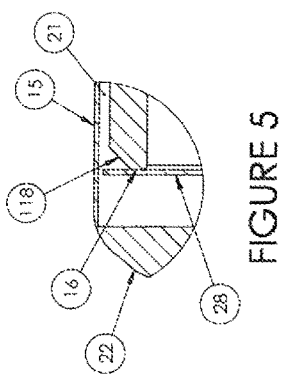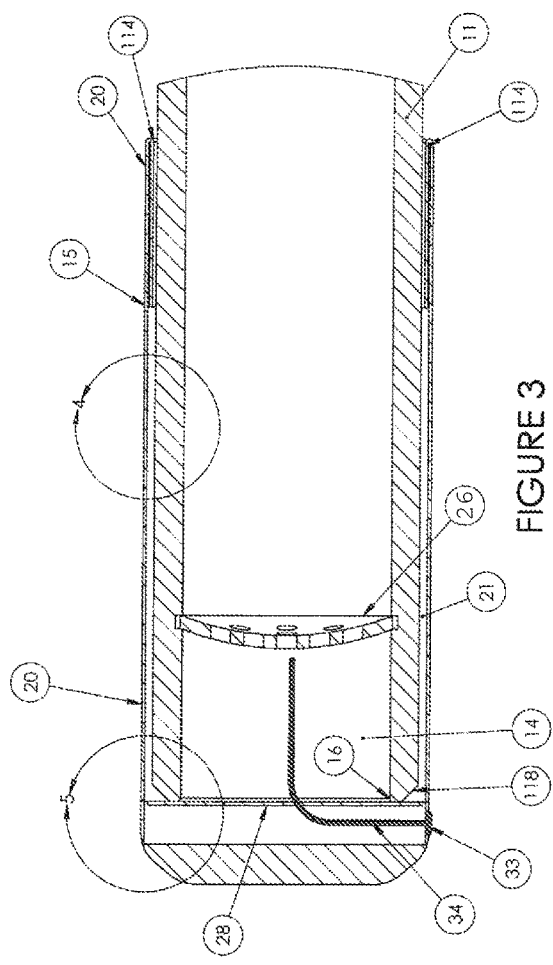

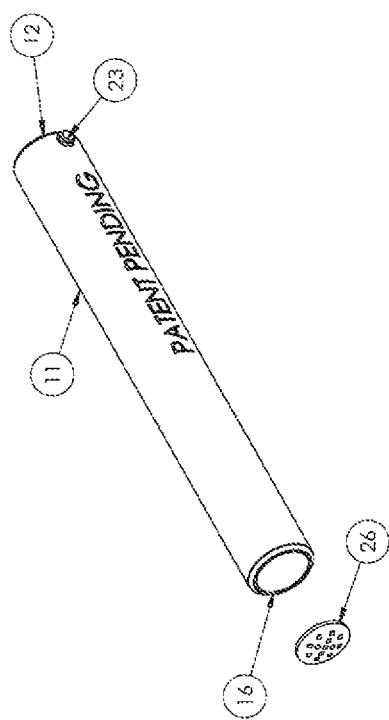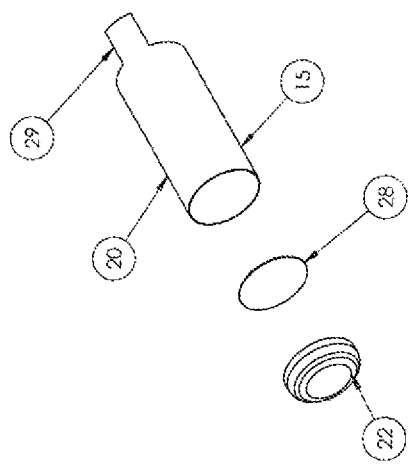
FIGURE 6

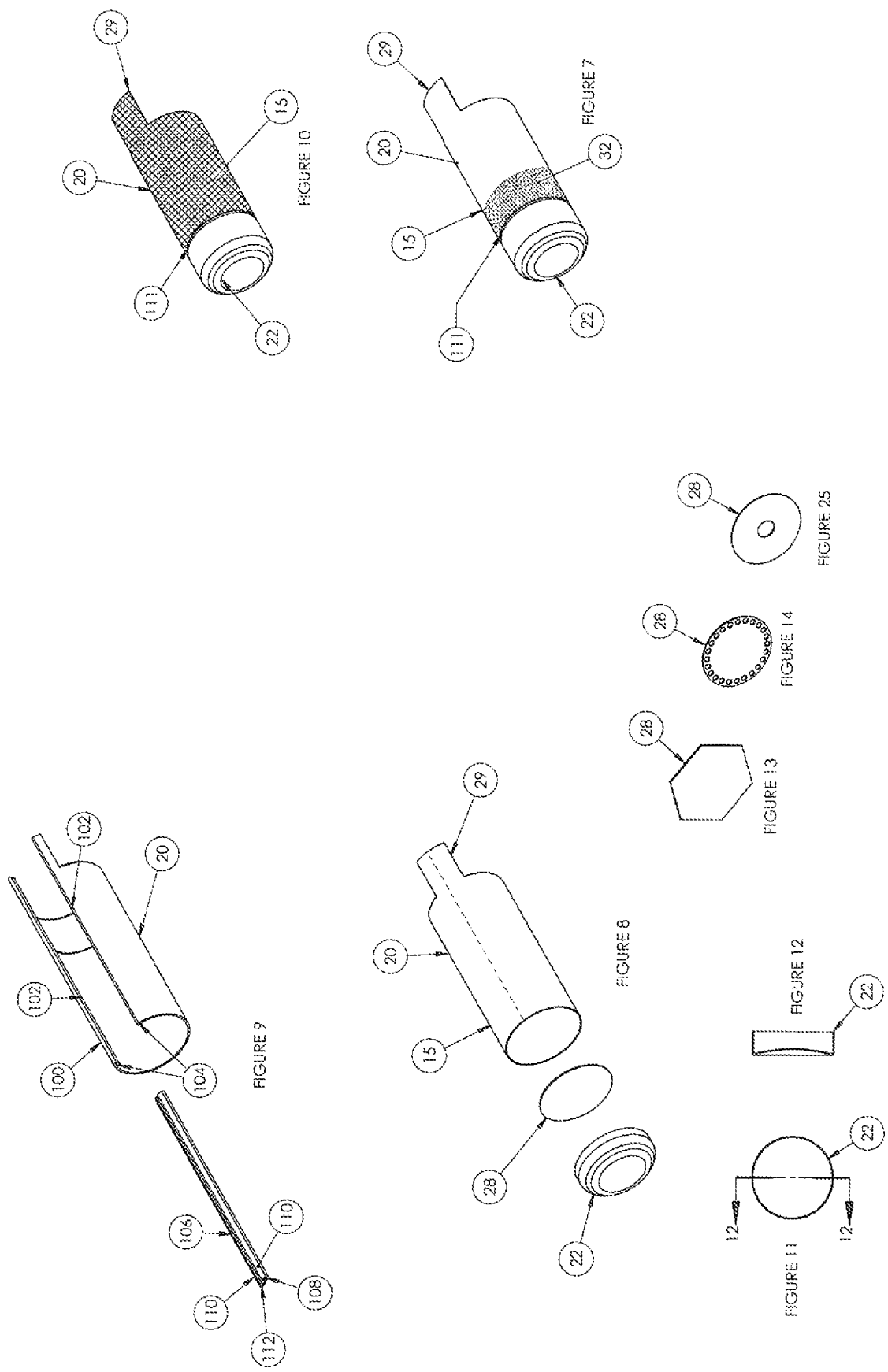

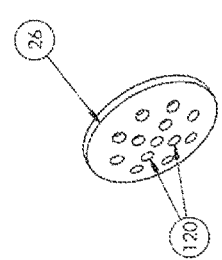
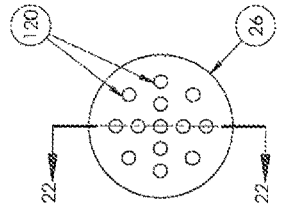
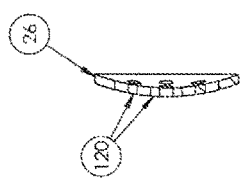
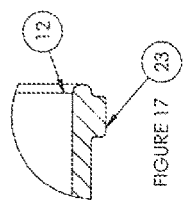
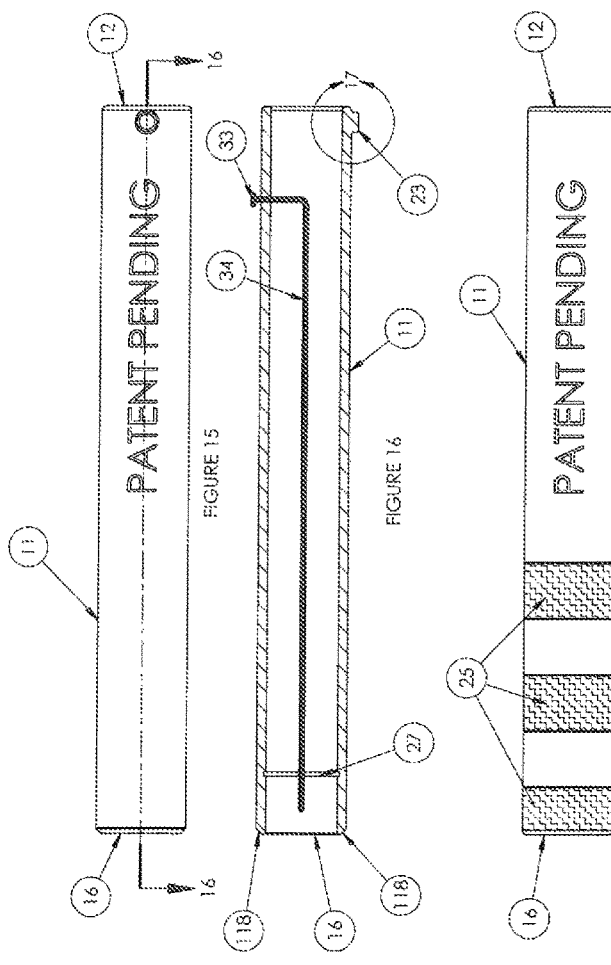
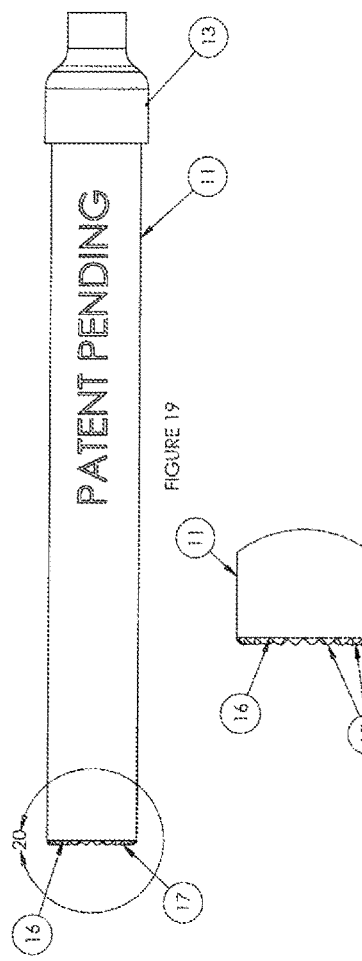

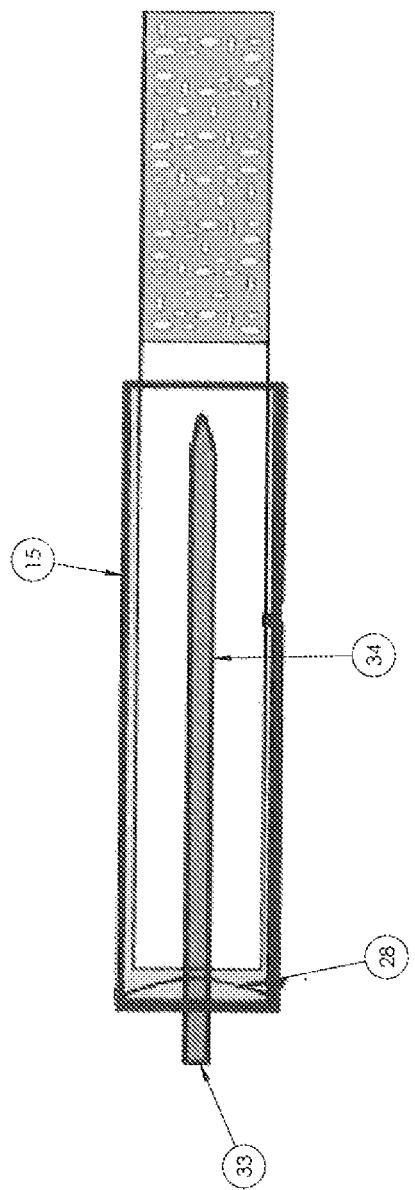

METHOD OF VOLATIZING A SUBSTANCE

RELATED APPLICATIONS

This application is a division application of U.S. patent application Ser. No. 14/142,351 filed on Dec. 27, 2013, entitled "Tubular Volatizing Device," issued as U.S. Pat. No. 11,213,073 on Jan. 4, 2022, the content of which is incorporated herein by reference.

FIELD OF THE INVENTION

The present invention relates generally to a volatizing extraction device, and more specifically to a volatizing device with an activation indicator(s).

BACKGROUND OF THE INVENTION

There are many devices designed to selectively vaporize or volatilize selected compounds from material placed within the device. In these previous devices, the vaporization chamber in which the material to be vaporized is connected, positioned and or secured to a tube to facilitate the evacuation of the volatilized compounds from the sample. The chamber is heated by applying heat from a flame or an electric element directly to the chamber. When the desired temperature is reached the target compounds from the sample within the chamber are vaporized. Once the target compounds are apparently vaporized, suction applied to the tube draws the vaporized extract from the material out of the chamber and into the tube.

Some of the drawbacks of these prior art devices include: (1) the challenge to determine when the sample material contained within the chamber has achieved volatilizing temperature; (2) whether heat is over applied to the chamber and the material, resulting in the creation or release of undesired compounds or potentially burning the sample material creating combustion byproducts in addition to the release of these undesired compounds, along with; (3) the length of time it takes to heat the device and or material to reach volatizing temperature; and (4) there commonly is an uncontrolled release of vapor, potentially containing target compounds prior to extraction of target compounds; (5) the size, mass and cost of devices with any type of control. In addition, prior art vaporization devices do not have multi-function caps. Prior art devices that do not contain their own heat source have no means of regulating temperature. Further, prior art vaporization devices designed with thermostats also have a built in heat source controlled by the thermostat. As a result, these prior art devices are more complex, with significant additional cost and manufacturing complexity as well as increased size and weight added to the device, therefore making the prior art devices more expensive to produce and more prone to failure.

As a result it is desirable to develop a device capable of overcoming these deficiencies of the prior art.

SUMMARY

To that end, according to one aspect of the present disclosure a volatizing device is provided in which the device decreases the preparation and warm up time necessary to volatize the desired compounds from the material and additionally decreases the amount of material necessary to obtain the desired quantity of extract from the device because the cap keeps the vapor contained there is only a minute amount of vapor released unless suction is applied. In addition, the device provides a means for an accurate indication when the heat applied to the device reaches the proper level for the volatization of the desired compounds from material held within the device. The device of the present disclosure employs a heat source controlled by the user and an indicating mechanism with one or more of the following functions conveying tactile and audible thermo indications by utilizing a snap disk or other thermal indicator. The thermo-indicator is constructed of a material or in a manner enabling the indicator to provide an indication to the user of the volatizing device that the temperature within the device has reached a level sufficient to volatize the selected compound from the material contained within the device. Preferably, but not in every event or usage of the device or components thereof, the desired compound is volatized from the material without combusting the material to avoid the extraction of undesired compounds from the material, such as by limiting the temperature to that at which the desired compounds are volatized and extracted, but below the temperature at which the material undergoes combustion.

The tactile nature of the indicator in the device of the present disclosure allows for the conveyance of activation temperature in environments where audible and or visual only indicators would be less effective or desirable. A slightly more complex design of the new device could incorporate a thermistor, or other solid state or mechanical indicator such as a magnet assembly, thermocouple, or thermal pile which will create a visual, audible, vibrational, mechanical, electrical, tactile or other signal to indicate proper temperature. The tactile, vibrational or kinesthetic nature of the described indicator allows for accurate use in loud, dark, bright or other environments where devices with visual or audible only indicators would be undesirable or difficult to be conveyed by the device or detected by the user. In other embodiments, the cap can function independent of the body as well as functioning without the thermal indicator and or other heat transference related components, but to a lesser degree of accuracy and higher propensity of over and or under extraction including a more likely initiation of combustion.

According to another aspect of the present disclosure, the above-described device can utilize a multitude of different heat sources of widely varying intensities and sources accurately and easily to achieve the same resultant extraction. Other examples of potential heat sources include but are not limited to solar radiation, induction heating, exothermic chemical reactions, friction, electricity, gas compression, flames, combustion, infrared radiation, and thermal conduction from a hot surface, fluid or gas. In order to enable the heat applied to the device from the various heat sources to be effectively transferred to the material held within the device in a controlled manner, there are several routes of transfer incorporated within the structure of the device of the present disclosure.

According to another aspect of the present disclosure, a method of volatizing a substance with a volatizing device is disclosed.

Numerous other aspects, features, and advantages of the present disclosure will be made apparent from the following detailed description together with the drawing figures.

BRIEF DESCRIPTION OF THE DRAWINGS

The drawings illustrate the best mode currently contemplated of practicing the present disclosure.

In the drawings:

FIG. 1 is a side plan view of one embodiment of a volatizer constructed according to the present disclosure;

FIG. 2 is a cross-sectional view along line 2-2 of FIG. 1;

FIG. 3 is a sectional view along line 3-3 of FIG. 2;

FIG. 4 is a sectional view along line 4-4 of FIG. 3;

FIG. 5 is a sectional view along line 5-5 of FIG. 3;

FIG. 6 is an exploded isometric view of the device of FIG. 1;

FIG. 7 is an isometric view of one embodiment of the cap for the device of FIG. 1;

FIG. 8 is an exploded view of the cap of FIG. 7;

FIG. 9 is an exploded view of an extractor used with the cap of FIG. 7;

FIG. 10 is an isometric view of a second embodiment of the cap of FIG. 7;

FIG. 11 is a front elevation view of a second embodiment of a cover used with the cap of FIG. 7;

FIG. 12 is a cross-sectional view along line 12-12 of FIG. 11;

FIG. 13 is an isometric view of a second embodiment of an indicator utilized with the cap of FIG. 7;

FIG. 14 is an isometric view of a third embodiment of an indicator utilized with the cap of FIG. 7;

FIG. 15 is a side elevation view of a first embodiment of a tube used with the device of FIG. 1;

FIG. 16 is a cross-sectional view along line 16-16 of FIG. 15;

FIG. 17 is a sectional view along line 17-17 of FIG. 16;

FIG. 18 is a side elevation view of a second embodiment of the tube of FIG. 15;

FIG. 19 is a side elevation view of a third embodiment of the tube of FIG. 15;

FIG. 20 is a sectional view along line 20-20 of FIG. 19;

FIG. 21 is an isometric view of one embodiment of a diffuser disc used with the device of FIG. 1;

FIG. 22 is a front elevation view of the disc of FIG. 21;

FIG. 23 is a cross-sectional view along line 23-23 of FIG. 22;

FIG. 25 is an isometric view of an indicator utilized with the cap of FIG. 24; and FIG. 26 is a cross-sectional view of a third embodiment of the device of FIG. 1.

DETAILED DESCRIPTION OF THE DISCLOSURE

Figure 24:
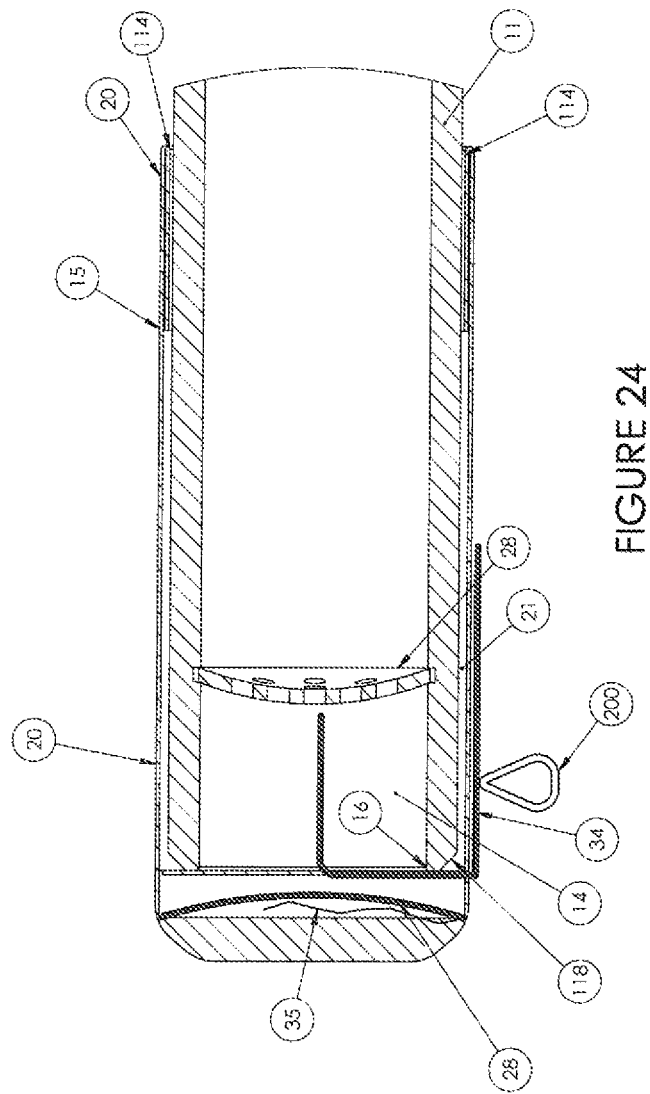
FIG. 24 is a cross-sectional view of a second embodiment of the device of FIG. 1.

Referring now in detail to the drawing figures, wherein like reference numerals represent like parts throughout the several views, one embodiment of a volatizer constructed according to the present disclosure is illustrated generally at 10 in FIG. 1. The volatizer 10 includes a body or tube 11 that is formed of any suitable material, such as glass, ceramic, metal or composite, inorganic composite, among others, and is generally tubular but not necessarily round in shape. Shapes may be but are not limited to triangular, square or rectangular. In one embodiment, the body 11 is formed of glass in order to enable the body 11 to retain and diffuse heat from the heat source 200, such as a lighter or flame, applied to the body 11 and the cap 15 at the heat ring(s) 32 or hot spot(s) 33. The heat ring(s) 32 or hot spot(s) 33, is a marking, and or location identified as the best area to apply heat to facilitate the best transfer of heat form the heat source 200 to the chamber 14 and the material 24. There may be a protrusion of another device or object as the heat ring(s) 32 or hot spot(s) 33. This device or object functions as a thermal conduit(s) or heat pipe(s) 34 to accelerate and improve heat flow. As best shown in FIGS. 1, 2, 6 and 15-20, the body 11 can additionally be formed with design elements such as an oval or non-round tube, bent tube, and/or can include tube appendages or protrusions 23 or other grip enhancing ribs or features 25 positioned on the exterior of the tube 11 to reduce the propensity to roll when placed on a flat surface, to improve grip on the body 11 or to add visual interest and/or improve aesthetics of the volatizer 10 without affecting the ability of the volatizer 10 to provide the desired function. The body 11, cap 15, or tip 13 may also have hole(s) and or perforations (not shown) with or without spring loaded or non-spring valve mechanisms (not shown) to function as flow rate regulators. These openings would allow air to bypass or flow around the chamber 14 and indicator 28. These openings serve several functions including the dilution of the extract from the chamber 14 and material as well as allowing for regulated vacuum/suction and or pressure on the chamber 14 and the cap 15. This arrangement allows for the device to self regulate the flow rate of air through the cap 15, chamber 14 and material 24 for a more consistent extraction at different levels of suction. While the illustrated embodiment shows the body 11 having a consistent diameter along its entire length, in other embodiments the volatizer body 11 may have differently sized, shaped and configured entry ports 16 and exit ports 12.

Additionally, the tube 11 can be formed or fabricated with serrations 17 (FIGS. 19 and 20) on the end of the tube 11 including the entry port 16 around the periphery of the entry port 16 or any portion thereof that can expedite processing, insertion and compaction of material 24 being prepared for volatizing. The serrations facilitate the processing of the material by cutting and grinding the material as the body 11 is twisted and pushed through a volume of the material. This feature significantly reduces the amount of preparation required before use, allowing most plant based as well as many other synthetic materials to be processed and inserted into the device quickly. As best shown in FIG. 19, the volatizer 10 may also include a suction tip 13 constructed of a variety of suitable materials such as silicone, metal, composites, ceramic, wood, glass or other polymers or thermoplastics, as desired. The tip 13 is positioned on the outlet or suction end, or exit port 12, of the tube 11 to facilitate the ability of a user to inhale or otherwise extract the volatized vapor components through the tube 11. The tip 13 can have any desired shape and can be permanently or removably secured to the outlet end 12 of the tube 11 in any suitable manner. or formed in place as an integral component of the body 11. The tip 13 may also incorporate a type of valve to further reduce the loss of vapor and or extract prior to suction being applied.

Opposite the tip 13, the volatizer 10 includes a cap 15, best shown in FIGS. 1-10. The cap 15 can be constructed in a variety of different methods from any number of suitable materials, such as metals, including suitable magnetic and appropriate non-magnetic alloys optimized for induction heating or thermally stable composite and or non metallic components with the necessary heat resistance and transfer properties to operate the volatizer 10. These materials can be formed into the desired shape for the cap 15 in any suitable manner or method, including deep drawing to produce a monolithic construction with a variable wall thickness and geometry or an assembly constructed from several fabricated components. It is also possible to produce the cap 15 or its components by growing the components through a method of deposition such as electroless deposition or chemical vapor deposition or by metal spinning or a combination of these described techniques. As best shown in FIG. 9, in one embodiment the cap 15 is formed with a collar 20 having a body 100 including a pair of opposed edges 102 each having an inwardly extending flange 104 positioned along the entire or at least a portion of the length thereof. The flanges 104 are engaged with a sleeve or drive 106 formed of a suitable material and having a central portion 108 and a pair of opposed locking tabs 110 on each side of the central portion 108. The flanges 104 are urged or moved towards one another to a position where the flanges 104 can be slid into the channel 112 defined between the locking tabs 110 and the central portion 108 to hold the flanges 104 in the closed configuration to form the collar 20 of the cap 15.

In embodiments where the cap 15 is not formed as a single piece of material, the cap 15 is closed at one end by a cover 22. The cover 22 can be formed as desired, and in the illustrated embodiments is shown as having a convex shape (FIGS. 7, 8 and 10) or a concave shape (FIGS. 11-12), but may also be flat. All parts and assemblies of the cap 15, body 11 can be textured, engraved, marked, embossed or otherwise modified in a manner to improve strength, heat retention, transference or simply aesthetics.

The cap 15 also includes an indicator 28 best shown in FIGS. 3, 5, 8, 13 and 14, that is formed either entirely or partially of a material that deform(s) or changes in some manner when heated to a predetermined temperature, such as a thermostat material including but not limited to a bimetal material. The indicator 28 is held within the cap 15 by securing the indicator 28 within the cap 15 or another location on or in the device 10, in any suitable manner, such as by welding or adhering the periphery or portions thereof of the indicator 28 in engagement with a groove or rib 111 formed on the interior surface of the cap 15 or by mechanically or frictionally fixing the periphery or portions thereof of the indicator 28 to the cap 15 or the cover 22, such as by engaging an inwardly extending retention rib 111 (FIG. 7) or between the cap and the cover 22. The use of a spring 35 can assist to further enhance or improve tactile feedback and or heat transfer to the indicator. The indicator 28 may also be constructed from a magnetic assembly, which upon reaching a set point temperature, as determined by the construction of the indicator 28, allows an engagement or disengagement of the indicator 28 with the cover 22 and/or cap 15 or other part of the device 10 due to the reduced magnetic strength of the heated magnet or in combination with a thermostat/bimetal spring or element. Additionally, the indicator 28 can be formed to be circular in shape, as shown in FIGS. 6 and 8, to conform to the shape of the cap 15, but can have any suitable shape including but not limited to ovals, triangles, diamonds, stars, octagons, pentagons, hexagons and other polygons as well as square, rectangular or other parallelograms or other configuration(s). In particular, the indicator 28 can be formed to have apertures 109 therein (FIGS. 14 and 25) or with a shape different than the internal shape of the collar 20, such as oblong, square or polygonal (FIG. 13), among others, and when the collar 20 is generally circular in cross-section. In this configuration, the spaces provided by the differences in the shapes of the indicator 28 and the collar 20 enable air to flow past the indicator 28. These embodiments also minimize contact of the indicator 28 with the cover 22 to decrease heat loss/gain and increase the accuracy of the activation of the indicator 28 relative to the selected internal temperature of the chamber 14.

In addition, the cover 22 can be formed at the outer end of the cap 15, with the thermo-indicator 28 spaced inwardly from the cover 22 along the collar 20. The cap 15 can also be formed from a single piece by deep draw, electrodeposition, or another means of forming a three-dimensional object from the material. The indicator 28, as best shown in FIG. 3, is either a smooth edged disc or one formed with a number of apertures 30 located at various locations around the indicator 28 in order to enable air flow around and or through the indicator 28. A central hole in the indicator 28 (FIGS. 24, 25) may also be utilized for the transit of a thermal conduit or heat pipe 34 as well as a means of retaining the indicator 28 in the correct position and or orientation on or around the conduit, tube and or heat pipe. Further, when the indicator 28 is spaced inwardly from the cover 22, the space between the indicator 28 and the cover 22 can be selected to enable the indicator 28 to contact the cover 22 and or the body 11 and or heat pipe 34 or any other part of the device when the activation temperature of the indicator 28 has been reached. In this manner, the indicator 28 is obscured by the cover 22, or other part of the device, the indicator 28 can provide an enhanced tactile indication upon reaching the selected temperature as a result of the contact created by actuation and contact of the indicator 28 with the cover 22 and or body 11 or other part of the device. The indicator 28 can also be retained in a manner, which allows for some freedom of movement. Another embodiment of the device 10 or the cap 15 may be constructed without the indicator 28, but retain some of the other features for heat exchange and or extraction.

The indicator 28 is configured to function as a thermo-indicator by audibly actuating or flexing itself or another mechanism or means of creating a tactile indication when heat applied to the cap 15 at or near the heat ring(s) 32 or hot spot(s) 33 through the body 11 causes the indicator 28 to reach a certain and specific predetermined temperature range determined by the material characteristics of the target compound(s) 19. The temperature of actuation can be a broad or very narrow range depending again on the target compounds 19. The temperature range in which the indicator 28 flexes and or indicates signaling it (the indicator 28) as well as the surrounding elements, cap 15, chamber 14, and material 24, has been heated to within the specified temperature range is set based on the composition of the indicator and/or the shape, thickness and or inherent stress in the indicator 28 present as a result of the fabrication of the indicator to be approximate to the temperature at which the desired compound 19 contained in the material 24 disposed within the chamber 14 is volatized from the material 24. The temperature range at which the indicator 28 triggers, flexes, deforms, or otherwise indicates is anticipated to be within a nominal range identified to be appropriate for the effective extraction of the target compound(s) 19 in order to enable the individual utilizing the volatizer 10 to selectively volatize the selected compound(s) or component(s) 19 which volatize or vaporize from the material 24 at a determined temperature range without also volatizing other compounds that are volatized at temperatures higher than are required for the selected compound.

Upon reaching the predetermined temperature, the flexing, deformation or actuation of the thermo-indicator 28 provides tactile, audible and or visual signals of the cap 15, chamber 14, material 24 and indicator 28 being heated to the desired temperature. A visual indication provided by the indicator 28 can be enhanced by the use of transparent or translucent materials in the portions of the body 11 having indicia (not shown) thereon of the temperature enabling visual orientation with the indicator 28 in the positions of the indicator 28 within and outside of the predetermined temperature range. In one embodiment, the flexing, or actuation of the indicator 28 can contact and additionally bow or deform the cover 22 outwardly from a flat or inwardly bowing position, providing the visual indication, while making a popping sound/vibration either by itself or in conjunction with the optional contact with the cover 22 and or body 11 to provide the audible and tactile indication. The cap 15 and or tube 11 may be constructed with elements such as heat ring(s) 32 or hot spot(s) 33, which serves as a means of indicating to the user where to apply the heat source as well as placement of a heat transference device, such as heat pipe(s) 34. Heat pipe(s) 34 can be incorporated in a variety of methods and manners to the device 10 including the cap 15 and the body 11 to facilitate rapid transference of heat from the heat source into the chamber 14 and the material 24. The heat pipe 34 promotes the transfer of heat from the heat source to the chamber via an evacuated tube containing an appropriate phase change fluid suitable for the temperature range necessary for the effective extraction of the target compounds 19 from the material 24. Highly conductive coatings, materials or elements such as synthetic graphite or the heat pipe 34 incorporated in the cap 15 or the tube 11 or both may also be used to facilitate the conduction and distribution of heat more uniformly from the heat source to the entire chamber 14 and the material 24 within the chamber 14. Another embodiment of FIG. 16 may place the chamber 14, the diffuser disc 26, the indicator 28 and any other component(s) of the device 10 in a different position to achieve the extraction such as placing the chamber 14 and the material 24 at the suction end 12, and reversing the flow through the diffuser disc 26.

The cap 15 is formed to be complementary in shape to the volatizer body 11, may include a collar 20 that is positioned around the body 11 with an inner diameter slightly larger than the outer diameter of the body 11 to define a space 21 therebetween, as shown in FIGS. 2-5, and a length sufficient to extend over the chamber 14 defined within the body 11. The collar 20 can be formed of any suitable material, such as a metal, in a manner to effectively and securely engage the cap 15 with the body 11. In the illustrated embodiment, when the cap 15 is positioned over the entry port 16 of the tube 11, to hold the cap 15 securely on the tube 11 such that the cap 15 does not inadvertently slide off of the tube 11, the collar 20 also includes one or more spacers 114 on the interior surface 116 opposite the cover 22, or utilizes another means of engaging the body such as an embossed texture. The texture which could be a geometric pattern or some sort of text, number, or other design, would function as a type of spring to allow not only a small amount of stretch over the body 11, but the texture would also allow a secure engagement onto a slightly smaller diameter tube. The spacers 114 and or the embossing enable the cap 15 to engage the exterior of the tube 11 to hold the cap 15 in the proper position on the tube 11, while also enabling airflow past the spacers 114 and into the space 21 between the cap 15 and the tube 11. The cap 15 can also optionally include an extractor device 29 protruding from the collar 20 or another part of the cap 15, either as an integrated element, or one added to the cap after the cap is fabricated, such as a heat pipe or pipes 34 that is or are in the illustrated embodiment slightly shorter in length than the depth of the chamber 14 from the chamber end 16 to the diffuser 26. The heat pipe(s) can be utilized in a variety of configurations including but not limited to bent, twisted, tapered, or straight, and may pass through the indicator 28 (FIG. 25) in one or more embodiments or be bent around the cap 14 and or indicator. When the cap 15 is removed from the tube 11, the extractor 29 can be inserted within the chamber 14 to facilitate the removal of the material 24 depleted of volatized target compound(s) 19 from within the chamber 14 without contacting and damaging the diffuser disc 26. The heat pipe(s) 34 may also function as a type of combination heat transfer device and extractor. These features may also play integral roles in the heat transfer and flow rate regulation of the device 10. Another embodiment of the volatizer 10 (FIG. 26) is a modified version of the cap 15 adapted for use with or without the body 11 to also function when placed, inserted and or affixed onto or over a cigarette or other product, including, but not limited to products and devices containing material traditionally extracted via combustion of the material intended for extraction or other means of extraction. The cap 15 in this embodiment functions in the same manner as described with or without one or more features and or elements such as a phase change heat pipe(s), hot air pipes, tubes or conduits or other type of thermal conduit to facilitate heat transfer from the heat source 200 to the material 24 for extraction of the target compounds 19, while also functioning as a means of preventing the initiation of combustion. The cap 15 in this configuration may utilize one or more of the indicators 28 also described, and may also be produced and used without an indicator 28.

Opposite the spacers 114, when the cap 15 is positioned on the tube 11, as best shown in FIGS. 3-5, the indicator 28 abuts the chamber end 16 of the tube 11. In the illustrated embodiment, the chamber end 16 includes a chamfer or taper 118 to minimize the contact between the end 16 and the indicator 28, allowing the indicator 28 to flex and/or deform freely without much interference from the end 16 while also allowing air flow between the indicator 28 and the end 16. Additionally, contact from the activation of the indicator 28 with the end 16 or any other part of the device can be used to produce and or enhance the tactile and audible indication resulting from the actuation of the indicator 28 against the end 16. The chamber end 16 can also have other suitable shapes, such as rounded on the interior and/or exterior surface, or tapered on the interior or interior and exterior surfaces.

Referring now to FIGS. 3, 16 and 21-23, when the cap 15 is placed on the tube 11 over the chamber end 16, the indicator 28 forms the outer end of the chamber 14 within which the material 24 to be extracted by volatizing and displacing the target compounds 19 is positioned. The inner end of the chamber 14 positioned within the interior of the tube 11 is formed by means of retaining and filtering the sample material 24 such as an integral retainer/diffuser disc 26 comprised of a noncombustible material spaced inwardly from the end 16, but disposed within the body 11 in a position inside the cap 15 when the cap 15 is in place over the entry or chamber end 16. In the illustrated embodiment, the disc 26 has a convex shape and is retained within the body 11 by a groove 27 formed in the body 11 and within which the disc 26 can be positioned. This diffuser disc 26 includes a number of apertures 120 formed therein that enable air flow through the apertures 120 from the chamber end 16 to the suction end 12 of the tube 11 and can be positioned in a variety of different positions and distances from the end 16. The spacing and positioning of the diffuser disc 26 and its holes, slots and their spacing and positioning may also play a role in the regulation and distribution of heat and airflow. The hole and or slot configurations can range from very small laser cut slits or holes, to inscribing pictures, logos, geometric patterns, as well as embossing, etching engraving or other markings, etc. The diffuser disc 26 also functions as a material stop or obstruction to retain the material 24 in the chamber 14 during loading, use and extraction. The convex shape of the diffuser disc 26 permits a secure placement in the internal groove 27 with an increasing force of engagement as pressure is applied from the insertion of material 24 into the chamber 14. In an alternative embodiment, the disc 26 can be formed as a part of and integral to the body 11.

Additionally, one or more portions of the cap 15 or the body 11 can include a coating material 202 or other type of heat transfer medium thereon that enhances absorption, conduction and thermal transfer from the heat source to the indicator 28, device 10 and material 24, such as an absorptive oxide coating, or an ionic fluid heat dispersant incorporating low temperature phase change. The use of one or more types of phase change materials in the design allows for the latent heat of fusion or vaporization to accelerate heat transfer as well as to prolong the time the chamber 14 and its material 24 are able to remain at the ideal extraction temperature without further application of heat. Phase change materials also assist in the temperature regulation of the device during warm up, by changing phase and limiting temperature rise at phase change, or after a given quantity of phase change material has been transferred from the heat source 200 to the chamber 14. Matching the phase change temperature, quantity of phase change material and the indicator 28 actuation temperature can improve accuracy and usability. The body 11 of the volatizer 10 or the cap 15 can also be provided with the capacity or a suitable structure (not shown) thereon that enables a handle or attachment of a heat source 200 to be secured to the body 11 to allow the user to more easily hold the body 11 and apply the heat with one hand, such as magnetic, or other type retainers to allow attachment to the heat source 200.

In use, initially the material 24 is placed through the end 16 within the chamber 14 in the tube 11 against the disc 26. The cap 15 is then placed over the end 16 of the tube 11 in a position where the indicator 28 engages the end 16, thereby positioning the collar 20 of the cap 15 over the entire chamber 14 and material 24 held therein. A suitable heat source 200 is then applied to the body 11 and the cap 15 at or near the heat ring(s) 32 or hot spot(s) 33. The heat supplied by the heat source 200 is transferred through the cap 15 and body 11 and or heat pipe(s) 34 to the indicator 28 and the material 24 to heat and volatize the selected components 19 of the material 24. The heat pipe(s) 34 may protrude from the body 11 or cover end 22 of the cap 15 in a manner where the heat source 200 applies heat only to the heat pipe(s) 34.

When the predetermined temperature range is reached, the indicator 28 flexes or deforms or otherwise indicates to provide the tactile (vibration), audible (snap), and/or visual (different position of the indicator in the tube) indication that the volatizing temperature for the target compounds 19 for the material 24 has been reached. At that point the heat source 200 is removed and the user can draw air through the suction port end 12/suction tip 13. The suction applied to the body 11 via the end 12 functions to draw air between the collar 20 of the cap 15 and the body 11 past the spacers 114 where it is warmed in the space 21 defined between the cap 15 and the body 11 by the heat retained by both the body 11 and the cap 15, which functions as an annular heat exchanger. The heated air subsequently flows from the space 21 into the chamber 14 between and/or through the indicator 28 and the end 16 of the body 11 and through the material 24 disposed in the chamber 14. The heated airflow correspondingly heats, volatizes and displaces the volatized extract 25 and target compounds 19 through the retainer/diffuser disc 26, which also retains any unvolatized material particles 24 in the chamber 14. It is at least in part the heating of the air as it passes through the annular space 21 between the collar 20 of the cap 15 and the tube 11 and the contact of the heated air with the material 24, which assists in heating the material 24 promoting the volatilization as well as the displacement of the desired compound(s) 19, 25. There is also some direct heating of the material 24 through the cap 15 and the body 11 heated through conduction. This arrangement also allows for a separation from any of the combustion by products or other contamination produced by or near the heat source 200, as well as substantially reducing the propensity of the heat source to initiate combustion of the sample material 24.

If at any time during the use of one embodiment of the device 10 the temperature of the indicator 28 drops below the predetermined temperature range, the indicator 28 can be designed to provide a further indication of this temperature drop by returning to the un-flexed, un-deformed or un-actuated original position, thereby giving a second tactile, audible and/or visual indication of the temperature change. The user can then stop applying suction to the end 12, and re-apply the heat source 200 to the cap 15 at the heat ring(s) 32 or hot spot(s) 33 until the indicator 28 provides still another indication that the desired temperature for the volatization of the target compounds) 19 for the material 24 has been reached.

Another embodiment uses a single actuating single use indicator 28. One use of this design is to facilitate the administration of medications through the use of a sterile, single use disposable device 12. Containing the medication in this type of dispenser can also reduce the likelihood of abuse and or cross contamination as additional measures can be employed to prevent the contained medication from being dispensed with the use of specific equipment. The use of an induction heat source is one example of a tamper resistant method of applying activation heat through an insulated device. Medications suitable for use in this type of device are ones commonly administered via a pulmonary route, but may also include many others administered in other manners. This route is advantageous in the rapid uptake by the patient. Pain medications for example could be given within seconds without the need for the insertion of an IV. Other types of currently difficult, undeveloped and or impossible to administer types or combinations of pharmaceuticals may lend well to this type of administration as the heat component may keep some difficult compounds stable until they are rapidly absorbed. Another advantage of this embodiment as well as the re-useable versions also described herein is the elimination of the environmentally harmful, and un-healthy synthetic fluorocarbon propellants currently utilized in inhaler type devices.

Another embodiment would have the disposable single use device 10 incorporating a preloaded dose of medication inside a non-removable cap. This medication would then be released and or made available for administration upon the heating of the device 10 until the indicator 28 actuated. Some medications being of a sensitive and or fragile or reactive nature may require a hermetically sealed device, which could be activated, by the actuation of the indicator 28, or the application of the heat with the indicator 28 signifying sufficient temperature is present to permit accurate and predictable dosing.

Another embodiment is a device 10 designed for insertion into an air freshener type appliance. This usage would allow the user the option of using their own source of fragrance by inserting their choice of material 24 into the device 10 and placing the device 10 into the appliance for a controlled release into the environment where the fragrance is desired. This option gives the user the ability to enjoy fragranced spaces in their environment without the need to resort to the traditional chemical methods utilized by fragrancing devices, sprays, and other synthetic means of changing the olfactory impact of a space.

Heat may also be applied via a variety of other devices specifically designed around these devices 10 as a means of quickly and accurately heating the device to operating temperature using any of the previously described heat sources and or methods.

When the material 24 has been extracted to the point where the desired compounds 19, 25 have been depleted from the material 24, the device 10 is allowed to cool and the cap 15 can be removed from the body 11. The extractor 29 can be used to facilitate the removal of any unvolatized material from within the chamber 14 to enable a fresh amount of material 24 to be positioned within the chamber 14. Additionally, as opposed to utilizing the extractor 29, the tube 11 can simply be vertically positioned and optionally tapped by or against an object (not shown) to dislodge the material 24 from within the chamber 14.

In an alternative embodiment for the device 10, the body 11 can employ as a heat source 200 a flameless catalytic hydrocarbon burner (not shown) into the cap 15, which would surround the cap 15 and increase the rate of heat transfer and reducing warm up time. This burner could still be fueled externally by a heat source 200 such as a standard butane cigarette lighter as it can inject the fuel into the cap 15 and burner assembly. When used as the heat source 200, the flameless burner could be ignited either electronically, by piezoelectric, or with the typical flash from a standard butane lighter.

In still another alternative embodiment of the device 10, the diffuser disc 26 can be positioned in the body 11 at a location that enables the tobacco containing portions of standard diameter cigarettes to be inserted into the chamber 14 as the material 24 to be volatized. In doing so, the cap 15 is removed and the cigarette is inserted into the chamber 14 until contacting the disc 26. In this position, the filter portion of the cigarette would be disposed outside of the body 11 and could be removed in any suitable manner thereby allowing the cap 15 to be positioned over the tube or body 11 to enable the device 10 to be utilized to volatize the target compound(s) 19, 25 within the tobacco portion of the cigarette.

As an altered version of this embodiment, as best shown in FIG. 24, the cap 15 can be formed with the indicator 28, which can optionally be present, attached to the cover 22 of the cap 15. The cap 15 also includes the heat tube 34 which is partially positioned along the exterior of the cap 15 and extends into the interior of the cap 15. In this position, the heat pipe 34 can contact the material 24 positioned within the chamber 14 such that a heat source 200 applied to the heat pipe 34 effectively heats the material 24 in the chamber 14. Additionally, in this embodiment (FIG. 26), the object containing the material to be at least partially volatized, which in previous embodiments is the body 11, can be other than the body 11, such as a cigarette (not shown), which has a diameter similar to that of the body 11 and can be inserted directly into the open end of the cap 15 with the tobacco portion of the cigarette contacting the portion of the heat pipe 34 disposed within the cap 15. In this configuration, the heating of the heat pipe 34 effectively heats the tobacco in the cigarette, optionally without burning the tobacco similarly to the option in all of the embodiments of this disclosure, to release the desired components 19, 25 from the tobacco, which functions as the material 24 in this embodiment.

In still another embodiment, the indicator 28 can be spaced from the end 16, or placed in a location other than in the cap 15 such as internal to the body 11, in place of the diffuser 26 or wherever the indicator could perform its intended function properly when the cap 15 is positioned on the tube 11, and a separate engaging structure on the cap 15 is used to properly position the cap 15 on the tube 11. In this or any other embodiment, the cap 15 and/or tube 11 can include a conical exterior end (not shown) built into the end of the cap 15 and/or tube 11 which could help amplify the snap/click sound generated by the movement of the indicator 28.

Another embodiment may include the device 10 without an indicator 28, and a number of the other described heat transfer, heat exchange, extraction, or other construction methods.

Various other embodiments of the present invention are contemplated as being within the scope of the filed claims particularly pointing out and distinctly claiming the subject matter regarded as the invention.

What is claimed is:

1. A method of volatizing a substance, the method comprising:
   providing a volatizer comprising:
   a body having a first end and a second end opposite and spaced from the first end, the first end comprising an open end accessible to a volatization chamber configured to retain a sample material therein containing target compounds for volatization, the second end of the body comprising a suction tip; and
   a multi-functional cap formed of a hollow cylinder secured over the open end on the first end of the body, the cap including a thermo-indicator within the hollow cylinder configured to provide an indication upon heating of the cap to or within a preselected temperature range of optimal volatilization and extraction conditions for the target compounds from the sample material, wherein the cap has an inner diameter larger than an outer diameter of the body and a number of spacers positioned on an interior surface of the cap that extend radially inwardly from the cap between the cap and the body to engage the body and define an airflow space between the cap and the body;
   wherein the multi-functional cap comprises a closure of the volatization chamber, a heat exchanger, an indicator housing, an indicator protector, and a susceptor for reactivity in an induction field; and
   applying an induction heat source to at least one of the body and the cap until the thermo-indicator provides an indication of the preselected temperature range of optimal volatilization and extraction conditions for the target compounds from the sample material.

2. The method of claim 1, further comprising applying suction to the second end of the body after applying the induction heat source to the cap.

3. The method of claim 2, further comprising:
   removing a depleted sample material from the body after applying the suction to the second end of the body; and
   replacing with a second sample material within the body.

4. The method of claim 3, wherein removing the depleted sample material comprises:
   removing the cap from the body to expose the depleted sample material; and
   removing the depleted sample material from the volatization chamber.

5. The method of claim 2, wherein applying the suction to the body comprises:
   drawing air between the cap and the body to preheat the air flow;
   drawing the preheated air flow through, around, or across the thermo-indicator into contact with the sample material;
   volatizing the target compounds of the sample material using the preheated air flow and conducted heat; and
   drawing the target compounds out of the sample material through the second end.

6. A method of volatizing a substance, the method comprising:
   providing a volatizer comprising:
   a body having a first end and a second end opposite and spaced from the first end, the first end comprising an open end accessible to a volatization chamber configured to retain a sample material therein containing target compounds for volatization, the second end of the body comprising a suction tip; and
   a cap formed of a hollow cylinder secured over the open end of the body, the cap including a thermo-indicator within the hollow cylinder configured to provide an indication upon heating of the cap to or within a preselected temperature range of optimal volatilization and extraction conditions for the target compounds from the sample material, wherein the thermo-indicator is positioned within and extends across an interior of the cap, wherein the cap further includes a texture at a location to engage the body upon insertion of the body into the cap, and wherein the thermo-indicator provides the indication upon heating to or within the preselected temperature range by deforming the thermo-indicator, the cap being constructed of a thermally conductive material; and
   applying an induction heat source to at least one of the body and the cap until the thermo-indicator provides an indication of the preselected temperature range of optimal volatilization and extraction conditions for the target compounds from the sample material.

7. The method of claim 6, further comprising applying suction to the second end of the body after applying the induction heat source to the cap.

8. The method of claim 7, further comprising:
   removing a depleted sample material from the body after applying the suction to the second end of the body; and
   replacing with a second sample material within the body.

9. The method of claim 8, wherein removing the depleted sample material comprises:
   removing the cap from the body to expose the depleted sample material; and
   removing the depleted sample material from the volatization chamber.

10. The method of claim 7, wherein the applying the suction to the body comprises:
    drawing air between the cap and the body to preheat the air flow;
    drawing the preheated air flow through, around, or across the thermo-indicator into contact with the sample material;
    volatizing the target compounds of the sample material using the preheated air flow and conducted heat; and
    drawing the target compounds out of the sample material through the second end.

* * * * *